United States Patent
Dorian et al.

(10) Patent No.: US 6,905,612 B2
(45) Date of Patent: Jun. 14, 2005

(54) PLASMA CONCENTRATE APPARATUS AND METHOD

(75) Inventors: Randel Dorian, San Diego, CA (US); Richard Wood Storrs, San Francisco, CA (US)

(73) Assignee: Hanuman LLC, San Francisco, CA (US)

( * ) Notice: Subject to any disclaimer, the term of this patent is extended or adjusted under 35 U.S.C. 154(b) by 259 days.

(21) Appl. No.: 10/394,828

(22) Filed: Mar. 21, 2003

(65) Prior Publication Data

US 2004/0182788 A1 Sep. 23, 2004

(51) Int. Cl.[7] .......................... B01D 37/00; B01D 15/02; B01D 24/00; B01D 29/00
(52) U.S. Cl. .................... 210/806; 210/219; 210/257.1; 210/416.1; 210/502.1; 210/649; 210/689; 422/44; 422/102; 435/2; 436/177; 436/178
(58) Field of Search .............................. 210/219, 257.1, 210/321.6, 416.1, 502.1, 649, 650, 651, 689, 782, 787, 806; 422/44, 102; 424/486, 488, 489, 530; 435/2; 436/177, 178

(56) References Cited

U.S. PATENT DOCUMENTS

| | | |
|---|---|---|
| 3,850,369 A | 11/1974 | Bull et al. |
| 3,897,343 A | 7/1975 | Ayers |
| 3,909,419 A | 9/1975 | Ayres |
| 3,931,018 A | 1/1976 | North, Jr. |
| 3,982,691 A | 9/1976 | Schultz |
| 4,046,699 A | 9/1977 | Zine, Jr. |
| 4,055,501 A | 10/1977 | Cornell |
| 4,077,396 A | 3/1978 | Wardlaw et al. |
| 4,187,979 A | 2/1980 | Cullis et al. |
| 4,322,298 A | 3/1982 | Persidsky |
| 4,416,654 A | 11/1983 | Schoendorfer et al. |
| 4,464,167 A | 8/1984 | Schoendorfer et al. |
| 4,675,117 A | 6/1987 | Neumann et al. |
| 4,776,964 A | 10/1988 | Schoendorfer et al. |
| 4,818,386 A | 4/1989 | Burns |
| 5,019,243 A | 5/1991 | McEwen et al. |
| 5,053,127 A | 10/1991 | Schoendorfer et al. |
| 5,131,907 A | 7/1992 | Williams et al. |
| 5,141,645 A | 8/1992 | Shiraki et al. |
| 5,147,290 A | 9/1992 | Jonsson |
| 5,165,938 A | 11/1992 | Knighton |

(Continued)

FOREIGN PATENT DOCUMENTS

| | | |
|---|---|---|
| EP | 1 079 224 A2 | 2/2001 |
| WO | WO 98/12274 | 2/1998 |
| WO | WO 99/67277 | 12/1999 |

*Primary Examiner*—John Kim
(74) *Attorney, Agent, or Firm*—William B. Walker (57) ABSTRACT

A plasma concentrator for producing plasma concentrate from a plasma from which erythrocytes have been substantially removed. The device comprises a concentrating chamber having an inlet port and an concentrate outlet, the concentrating chamber containing hydrogel beads and at least one inert agitator; and a concentrate chamber having an inlet communicating with the concentrator outlet through a filter, and having an plasma concentrate outlet port. A process for producing plasma concentrate from plasma from which erythrocytes have been substantially removed, comprising the steps of a) moving the plasma into a concentrating chamber containing hydrogel beads and an agitator to form a hydrogel bead-plasma mixture; b) causing the agitator to stir the hydrogel bead-plasma mixture, facilitating absorption of water by the beads from the plasma, until a hydrogel bead-plasma concentrate is formed; and c) separating the plasma concentrate from the hydrogel beads by passing the plasma concentrate through a filter. The concentrator can be one or more syringe devices coupled for multiple concentrations.

29 Claims, 6 Drawing Sheets

U.S. PATENT DOCUMENTS

| | | |
|---|---|---|
| 5,171,456 A | 12/1992 | Hwang et al. |
| 5,185,001 A | 2/1993 | Galanakis |
| 5,234,608 A | 8/1993 | Duff |
| 5,269,927 A | 12/1993 | Fiehler |
| 5,271,852 A | 12/1993 | Luoma, II |
| 5,318,782 A | 6/1994 | Weis-Fogh |
| 5,322,620 A | 6/1994 | Brown et al. |
| 5,344,752 A | 9/1994 | Murphy |
| 5,370,802 A | 12/1994 | Brown |
| 5,387,187 A | 2/1995 | Fell et al. |
| 5,403,272 A | 4/1995 | Deniega et al. |
| 5,456,885 A | 10/1995 | Coleman et al. |
| 5,494,578 A | 2/1996 | Brown et al. |
| 5,494,592 A | 2/1996 | Latham, Jr. et al. |
| 5,585,007 A | 12/1996 | Antanavich et al. |
| 5,601,727 A | 2/1997 | Bormann et al. |
| 5,607,579 A | 3/1997 | Latham, Jr. et al. |
| 5,614,106 A | 3/1997 | Payrat et al. |
| 5,649,903 A | 7/1997 | Deniega et al. |
| 5,707,331 A | 1/1998 | Wells et al. |
| 5,707,876 A | 1/1998 | Levine |
| 5,733,545 A | 3/1998 | Hood, III |
| 5,817,519 A | 10/1998 | Zelmanovic et al. |
| 5,833,866 A | 11/1998 | Brown |
| 5,834,418 A | 11/1998 | Brazeau et al. |
| 5,837,150 A | 11/1998 | Langley et al. |
| 5,863,892 A | 1/1999 | Stern et al. |
| 5,865,785 A | 2/1999 | Bischof |
| 5,899,874 A | 5/1999 | Jonsson |
| 5,900,245 A | 5/1999 | Sawhney et al. |
| 5,938,621 A | 8/1999 | Kelly et al. |
| 5,955,032 A | 9/1999 | Kelly et al. |
| 5,955,436 A | 9/1999 | Kunkle, Jr. |
| 5,958,250 A | 9/1999 | Brown et al. |
| 5,980,734 A | 11/1999 | Itoh |
| 6,010,627 A | 1/2000 | Hood, III |
| 6,022,306 A | 2/2000 | Dumont et al. |
| 6,025,201 A | 2/2000 | Zelmanovic et al. |
| 6,051,146 A | 4/2000 | Green et al. |
| 6,051,147 A | 4/2000 | Bischof |
| 6,053,856 A | 4/2000 | Hlavinka |
| 6,054,122 A | 4/2000 | MacPhee et al. |
| 6,063,624 A | 5/2000 | Kandler et al. |
| 6,071,421 A | 6/2000 | Brown |
| 6,071,422 A | 6/2000 | Hlavinka et al. |
| 6,071,423 A | 6/2000 | Brown et al. |
| 6,090,793 A | 7/2000 | Zimmermann et al. |
| 6,096,309 A | 8/2000 | Prior et al. |
| 6,117,425 A | 9/2000 | MacPhee et al. |
| 6,196,987 B1 | 3/2001 | Holmes et al. |
| 6,197,325 B1 | 3/2001 | MacPhee et al. |
| 6,200,287 B1 | 3/2001 | Keller et al. |
| 6,214,338 B1 | 4/2001 | Antanavich et al. |
| 6,245,900 B1 | 6/2001 | Yamasaki et al. |
| 6,280,400 B1 | 8/2001 | Niermann |
| 6,296,602 B1 | 10/2001 | Headley |
| 2002/0114775 A1 * | 8/2002 | Pathak .................. 424/78.17 |

\* cited by examiner

PLASMA CONCENTRATE APPARATUS AND METHOD

FIELD OF THE INVENTION

The present invention concerns devices and methods for making concentrated plasma. The present invention concerns apparatus and methods for separation and concentration of plasma and plasma platelet mixtures from plasma and is particularly applicable to the preparation and use of autologous plasma concentrates.

Rapid fractionation of blood into erythrocyte, plasma or plasma-platelet fractions is desirable for the preparation of autologous concentrates from blood obtained from a patient during surgery. Each fraction can be modified or returned to the blood donor. Useful plasma fractions, with our without platelets, have value as sealants when concentrated without precipitation of fibrinogen, that is, when concentrated by removal of water therefrom in accordance with this invention. This invention has particular value for rapidly preparing autologous concentrated plasma fractions to help or speed healing, or as a hemostatic agent or tissue sealant.

BACKGROUND OF THE INVENTION

Blood may be fractionated and the different fractions of the blood used for different medical needs. For instance, anemia (low erythrocyte levels) may be treated with infusions of erythrocytes. Thrombocytopenia (low thrombocyte (platelet) levels) may be treated with infusions of platelet concentrate.

Under the influence of gravity or centrifugal force, blood spontaneously sediments into layers. At equilibrium the top, low-density layer is a straw-colored clear fluid called plasma. Plasma is a water solution of salts, metabolites, peptides, and many proteins ranging from small (insulin) to very large (complement components). Plasma per se has limited use in medicine but may be further fractionated to yield proteins used, for instance, to treat hemophilia (factor VIII) or as a hemostatic agent (fibrinogen).

Following sedimentation, the bottom, high-density layer is a deep red viscous fluid comprising a nuclear red blood cells (erythrocytes) specialized for oxygen transport. The red color is imparted by a high concentration of chelated iron or heme that is responsible for the erythrocytes high specific gravity. Packed erythrocytes, matched for blood type, are useful for treatment of anemia caused by, e.g., bleeding. The relative volume of whole blood that consists of erythrocytes is called the hematocrit, and in normal human beings can range from about 38% to about 54%.

Depending upon the time and speed of the centrifugation, an intermediate layer can be formed which is the smallest, appearing as a thin white band on top the erythrocyte layer and below the plasma; it is called the buffy coat. The buffy coat itself generally has two major components, nucleated leukocytes (white blood cells) and a nuclear smaller bodies called platelets (thrombocytes). Leukocytes confer immunity and contribute to debris scavenging. Platelets seal ruptures in the blood vessels to stop bleeding and deliver growth and wound healing factors to the wound site. If the centrifugation is of short duration, the platelets can remain suspended in the plasma layer.

The sedimentation of the various blood cells and plasma is based on the different specific gravity of the cells and the viscosity of the medium. This may be accelerated by centrifugation according approximately to the Svedberg equation:

$$V=((2/9)\omega^2 R(d_{cells}-d_{plasma})r^2)/\eta_t$$

where
V=sedimentation velocity,
ω=angular velocity of rotation,
R=radial distance of the blood cells to the center of the rotor,
d=specific gravity,
r=radius of the blood cells, and
$\eta_t$=viscosity of the medium at a temperature of t° C.
Characteristics of blood components are shown in Table A.

TABLE A

| Component | Diameter (μm) | Specific gravity (g/ml) | Deformability | Adhesion |
|---|---|---|---|---|
| Red cells | 5.4 | 1.100 | +++ | − |
| Granulocytes | 9.6 | 1.085 | + | ++ |
| Lymphocytes | 7.6 | 1.070 | ± | ± |
| Monocytes | 11.2 | 1.063 | ± | + |
| Platelets | 3.2 | 1.058 | ± | +++ |
| Plasma | NA | 1.026 | NA | NA |
| Additive solution | NA | 1.007 | NA | NA |

When sedimented to equilibrium, the component with the highest specific gravity (density) eventually sediments to the bottom, and the lightest rises to the top. But the rate at which the components sediment is governed roughly by the Svedberg equation; the sedimentation rate is proportional to the square of the size of the component. In other words, at first larger components such as white cells sediment much faster than smaller components such as platelets; but eventually the layering of components is dominated by density.

Soft Spin Centrifugation

When whole blood is centrifuged at a low speed (up to 1,000 g) for a short time (two to four minutes), white cells sediment faster than red cells and both sediment much faster than platelets (per Svedberg equation above). At higher speeds the same distribution is obtained in a shorter time. This produces layers of blood components that are not cleanly separated and consist of (1) plasma containing the majority of the suspended platelets and a minor amount of white cells and red cells, and (2) below that a thick layer of red cells mixed with the majority of the white cells and some platelets. The method of harvesting platelet-rich plasma (PRP) from whole blood is based on this principle. The term "platelet-rich" is used for this component because most of the platelets in the whole blood are in the plasma following slow centrifugation so the concentration of platelets in the plasma has increased.

Centrifugal sedimentation that takes the fractionation only as far as separation into packed erythrocytes and PRP is called a "soft spin". "Soft spin" is used herein to describe centrifugation conditions under which erythrocytes are sedimented but platelets remain in suspension. "Hard spin" is used herein to describe centrifugation conditions under which erythrocytes sediment and platelets sediment in a layer immediately above the layer of erythrocytes.

Two Spin Platelet Separation

Following a soft spin, the PRP can removed to a separate container from the erythrocyte layer, and in a second centrifugation step, the PRP may be fractioned into platelet-poor plasma (PPP) and platelet concentrate (PC). In the second spin the platelets are usually centrifuged to a pellet to be re-suspended later in a small amount of plasma or other additive solution.

In the most common method for PRP preparation, the centrifugation of whole blood for 2 to 4 min at 1,000 g to 2,500 g results in PRP containing the majority of the platelets. After the centrifugation of a unit (450 ml) of whole blood in a 3-bag system the PRP is transferred to an empty satellite bag and next given a hard spin to sediment the platelets and yield substantially cell-free plasma. This is termed "two-spin" platelet separation.

To recover the platelets following two-spin separation, most of the platelet poor plasma (PPP) is removed except for about 50 ml and the pellet of platelets is loosened and mixed with this supernatant. Optionally one can remove about all plasma and reconstitute with additive solution. To allow aggregated platelets to recover the mixture is given a rest of one to two hours before platelets are again re-suspended and then stored on an agitator.

It is believed that two-spin centrifugation can damage the platelets by sedimenting the platelets against a solid, non-physiological surface. The packing onto such a surface induces partial activation and may cause physiological damage, producing "distressed" platelets which partially disintegrate upon resuspension.

Hard Spin Centrifugation

If the centrifugation is continued at a low speed, the white cells will sediment on top of the red cells whereas the platelets will remain suspended in the plasma. Only after extended low speed centrifugation will the platelets also sediment on top of the red cells.

Experiments with a blood processor have shown that centrifugation at a high speed (2,000 g–3,000 g) produces a similar pattern of cell separation in a shorter time. Initially the cells separate according to size, i.e., white cells sediment faster than red cells and platelets remain in the plasma. Soon the red cells get 'packed' on each other squeezing out plasma and white cells. Because of their lower density, white cells and platelets are pushed upwards to the interface of red cells and plasma whereas the platelets in the upper plasma layer will sediment on top of this interface, provided the centrifugal force is sufficiently high and sedimentation time is sufficiently long. Plasma, platelets, white cells and red cells will finally be layered according to their density. Platelets sedimented atop a layer of red cells are less activated than those isolated by the "two spin" technique.

Leukoreduction

The PC's resulting from both two spin processing and apheresis methods contain donor leukocytes. The white cells negatively affect platelet storage and may induce adverse effects after transfusion due to cytokine formation. Removal of leukocytes (leukoreduction) from PRP and PC is important because non-self leukocytes (allogeneic leukocytes) and the cytokines they produce can cause a violent reaction by the recipient's leukocytes. In 1999 the FDA Blood Product Advisory Committee recommended routine leukoreduction of all non-leukocytes components in the US (Holme 2000). Therefore, much of the prior art focuses on leukoreduction of platelet concentrates because non-autologous leukocytes excite deleterious immune reactions. Since the process of this invention provides a convenient way to quickly harvest autologous platelets from the patient's blood, immune reactions are not a risk, and the presence of leukocytes is of little or no concern.

Plasma concentrates and their utility in hemostasis and wound healing have been described in U.S. Pat. No. 5,585,007. Plasma concentrates can be made in a two-step method, first separating of plasma from the majority of erythrocytes and then concentrating the plasma by removing water. The plasma can be separated from the erythrocytes by centrifugation. The water can be removed from the plasma using a semipermeable membrane or by contact with a desiccated hydrogel bead. The membrane and hydrogel bead pores allow passage of water, salts and other low molecular weight components while blocking passage of cells, platelets (thrombocytes), cell fragments and larger molecules such as fibrinogen. The passage of water and low molecular weight components through the membrane or into the bead concentrates the plasma and the cells and high molecular weight components contained therein. The dry hydrogel beads can be dextranomer or polyacrylamide.

Recent publications report that platelet preparations enhance the healing rate of hard and soft tissue defects. Activated cytokine proteins, released from activated platelets, signal the migration, proliferation and activation of monocyte cells. Monocyte cells sense a gradient of cytokines and migrate towards the source.

Fibers of polymerized fibrin form pathways by which monocyte cells translocate into the wound. Translocation is enhanced by tension on these fibers imparted by the action of platelet microtubules during clot retraction. Therefore, in situ polymerization of platelet-containing fibrinogen solutions provides an enhanced setting for wound healing. Plasma concentrates containing platelets provide enhanced signals and pathways for wound healing cell migration.

Platelets have a limited half-time in vivo, and platelet activity declines rapidly ex vivo. An optimal wound-healing compound therefore would contain freshly isolated platelets. To minimize risk of disease transmission and maximize beneficial patient response to platelet activity the platelet/plasma concentrate would preferably be prepared from the patient's own blood, i.e. autologously. The amount of blood withdrawn from the patient should be as small as possible to minimize morbidity caused by blood loss.

The present invention provides methods and apparatus for rapidly contacting patient plasma with dry hydrogel beads, concentrating said plasma and separating the resulting plasma concentrate from the beads for application to patient wounds.

SUMMARY OF THE INVENTION

This invention includes a plasma concentrator for producing plasma concentrate from plasma from which platelets and erythrocytes have been substantially removed and for producing concentrate from platelet-rich plasma. The plasma concentrator can comprise a concentrating chamber having an inlet port and a concentrate outlet port, the concentrating chamber containing hydrogel beads and at least one inert agitator. The plasma concentrator also has a concentrate chamber having an inlet communicating with the concentrator outlet through a filter, and having a plasma concentrate outlet port. The agitator can be a dense object such as a smooth ball which can be stainless steel or other dense material with an inert surface which will not impair the blood proteins. The filter can be a porous frit.

One embodiment of this plasma concentrator comprises a syringe device, the syringe device including a syringe barrel with a proximal concentrating zone and a distal concentrate zone with an inlet/outlet port. A filter separates the concentrating zone from the concentrate zone, and a plunger is positioned for axial movement in the concentrating zone. Hydrogel beads and at least one agitator are positioned in the concentrating zone between the plunger and the filter. The agitator can be a dense object such as a smooth ball which can be stainless steel or other dense material with an inert surface which will not impair the blood proteins. The filter can be a porous frit. The syringe barrel has an inner wall surface, and the plunger can be a piston forming a sealing engagement with said inner wall surface.

Another embodiment of the plasma concentrator of this invention comprises first and second syringe devices. Each syringe device includes a syringe barrel with a proximal concentrating zone and a distal concentrate zone with an inlet/outlet port, and a filter separating the plunger zone from the concentrate zone. A plunger is positioned for axial movement in the proximal portion of the concentrating zone, and hydrogel beads and at least one agitator are positioned in the concentrating zone between the plunger and the filter. The inlet/outlet port of the first syringe communicates with the inlet/outlet port of the second syringe. The inlet/outlet ports can have a coupling for a plasma transfer syringe, and optionally, they can communicate through a check valve.

A process of this invention for producing plasma concentrate from plasma from which erythrocytes have been substantially removed, comprises (a) moving the plasma into a concentrating chamber containing hydrogel beads and an agitator to form a hydrogel bead-plasma mixture; (b) causing the agitator to stir the hydrogel bead-plasma mixture, facilitating absorption of water by the beads from the plasma, until a hydrogel bead-plasma concentrate is formed, and (c) separating the plasma concentrate from the hydrogel beads by passing the plasma concentrate through a filter. The hydrogel beads can have the effective absorption capacity to remove at least 10 percent of the water from the plasma, at least 25 percent of the water from the plasma or at least 50 percent of the water from the plasma.

In a modification of this process for producing greater concentration of the plasma, the plasma concentrate from step (c) is further processed by the steps of (d) moving the plasma concentrate into a second concentrating chamber containing hydrogel beads and an agitator to form a hydrogel bead-plasma mixture; (e) causing the agitator to stir the hydrogel bead-plasma concentrate mixture, facilitating further absorption of water by the beads from the plasma concentrate, until a more concentrated hydrogel bead-plasma concentrate is formed; and (f) separating the more concentrated plasma concentrate from the hydrogel beads by passing the more concentrated plasma concentrate through a filter.

In a process of this invention for producing plasma concentrate with a plasma concentrator using a syringe device, the syringe device includes a syringe barrel with a proximal concentrating zone and a distal concentrate zone having an inlet/outlet port. A filter separates the plunger zone from the concentrate zone, and a plunger is positioned for axial movement in the proximal portion of the concentrating zone. Hydrogel beads and at least one agitator are positioned in the concentrating zone between the plunger and the filter. The process comprises drawing plasma, from which erythrocytes have been substantially removed, through the inlet/outlet port and the filter, by axial movement of the plunger in the proximal direction away from the filter. Then (b) the syringe is moved in alternative distal and proximal directions along the central axis to stir the hydrogel bead-plasma mixture, facilitating absorption of water by the beads from the plasma, until a hydrogel bead-plasma concentrate is formed. Then (c) plasma concentrate is separated from the hydrogel beads by moving the plasma concentrate through the filter and into the concentrate chamber. In step (c) the plasma concentrate can be moved through the filter and into the concentrate chamber by moving the plunger in the distal direction toward the filter. Alternatively, the plasma concentrate can be forced through the inlet/outlet port by moving the plunger in the distal direction toward the filter. The hydrogel beads can have the effective absorption capacity to remove at least 10 percent of the water from the plasma, at least 25 percent of the water from the plasma, or at least 50 percent of the water from the plasma.

A process of this invention for producing plasma concentrate from whole blood comprising the steps of (a) removing erythrocytes from whole blood to form a plasma which is substantially free from erythrocytes; (b) moving the plasma into a concentrating chamber containing hydrogel beads and an agitator to form a hydrogel bead-plasma mixture; (c) causing the agitator to stir the hydrogel bead-plasma mixture, facilitating absorption of water by the beads from the plasma, until a hydrogel bead-plasma concentrate is formed; and (d) separating the plasma concentrate from the hydrogel beads by passing the plasma concentrate through the filter.

In a process of this invention for producing plasma concentrate from whole blood using a syringe device, the syringe device can include a syringe barrel with a proximal concentrating zone and a distal concentrate zone having an inlet/outlet port. A filter separates the plunger zone from the concentrate zone; a plunger is positioned for axial movement in the proximal portion of the concentrating zone; and hydrogel beads and at least one agitator positioned in the concentrating zone between the plunger and the filter. The process comprises (a) removing erythrocytes from whole blood to form a plasma which is substantially free from erythrocytes; (b) drawing plasma from which erythrocytes have been substantially removed through the inlet/outlet port and the filter, by axial movement of the plunger in the proximal direction away from the filter; (c) moving the syringe in alternative distal and proximal directions along the central axis to stir the hydrogel bead-plasma mixture, facilitating absorption of water by the beads from the plasma, until a hydrogel bead-plasma concentrate is formed; and (d) separating plasma concentrate from hydrogel beads by moving the plasma concentrate through the filter and into the concentrate chamber. In step (c) the plasma concentrate is moved through the filter and into the concentrate chamber by moving the plunger in the distal direction toward the filter. The plasma concentrate can be forced through the inlet/outlet port by moving the plunger in the distal direction toward the filter.

DETAILED DESCRIPTION OF THE INVENTION

The term "plasma" as used in this application includes plasma containing a substantial concentration of platelets and plasma that does not contain a significant concentration of platelets.

The apparatus and methods of this invention offer inexpensive streamlined systems for rapidly preparing plasma concentrates. The entire concentration process can be accomplished in less than ten minutes. The product can be cell-free plasma concentrate, or if desired, plasma concentrates containing platelets.

Figures 1, 2:
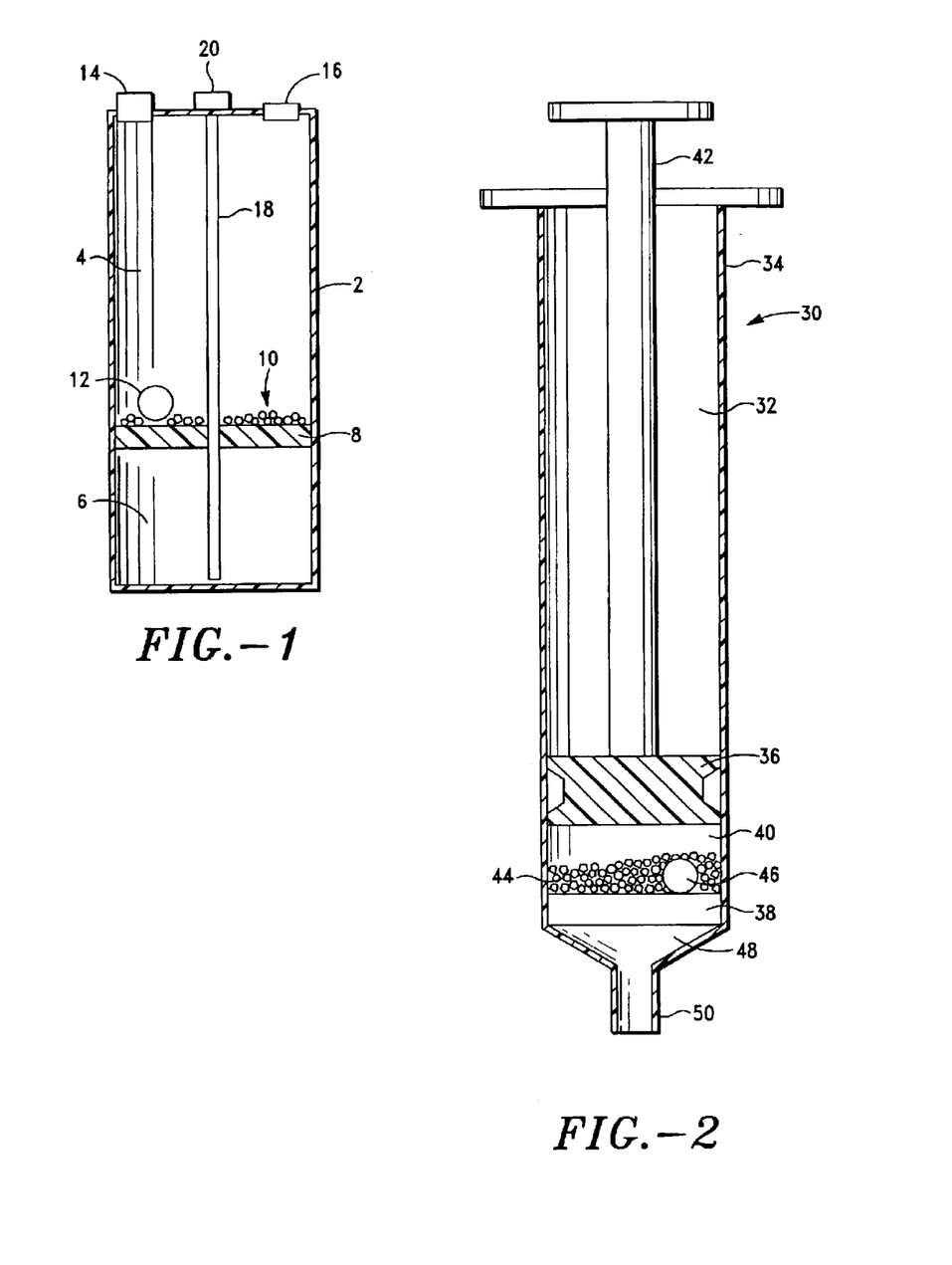
FIG. 1 is a cross-sectional schematic view of the apparatus of this invention for producing plasma concentrate from plasma.
FIG. 2 is a cross-sectional schematic view of a syringe embodiment of this invention for producing plasma concentrate from plasma.

FIG. 1 is a cross-sectional schematic view of the apparatus of this invention for producing plasma concentrate from plasma.

The concentrator comprises a concentrator vessel 2 having a concentrating chamber 4 and a concentrate chamber 6 separated from the concentration chamber 4 by a porous filter 8. Desiccated beads 10 and one or more agitators 12 are positioned in the concentrating chamber 4. A plasma inlet port 14 and an air vent port 16 communicate with concentrating chamber 4. Concentrate extraction tube 18 having an extraction port 20 extends into the concentrate chamber 4 and communicates therewith.

The device shown in FIG. 1 can be used to concentrate plasma by removing water from the plasma without precipitating fibrinogen. The plasma can be free of cells, or it can contain platelets. The method for concentrating plasma from which erythrocytes and plasma have been removed, without precipitating fibrinogen, comprises introducing plasma through port 14 into the concentrating chamber 4 where it contacts hydrogel beads 10 and an agitator 12, to form a plasma-hydrogel bead mixture. The plasma-hydrogel bead mixture is agitated by shaking the mixture in a reciprocal motion along the central axis (not shown) of the vessel 2, thereby repeatedly passing the agitator through the plasma-hydrogel mixture. Water is removed from the plasma by the hydrogel beads 10. The vessel 2 is then centrifuged to pass the plasma concentrate through the filter 8 and into the concentrate chamber 6. The liquid plasma concentrate is then drawn up the tube 18, for example with a syringe (not shown) attached to extraction port 20 to remove it from the concentrate chamber 6.

The desiccant hydrogel beads 10 are insoluble beads or disks which will absorb a substantial volume of water and do not introduce any undesirable contaminant into the plasma. They can be dextranomer or acrylamide beads which are commercially available (Debrisan from Pharmacia and BIO-GEL p™ from Bio-Rad Laboratories, respectively). Alternatively, other concentrators can be used, such as SEPHADEX™ moisture or water absorbants (available from Pharmacia), silica gel, zeolites, cross-linked agarose, etc., in the form of insoluble inert beads or discs.

The agitator 12 is a dense object which can be an inert metal sphere. It will be readily apparent to a person skilled in the art that the shape, composition and density of the agitator 12 can vary widely without departing from the invention so long as the agitator has a density substantially greater than hydrated hydrogel beads. It is advantageous that the agitator be a metal sphere such as a titanium or stainless steel sphere which will not react with blood components, or a dense sphere coated with an inert coating such as TEFLON which will not react with blood components.

The filter 8 can be any inert mesh or porous materials which will permit the passage of plasma and exclude the hydrogel beads and agitator. The filter can be a metal wire or inert fiber frit of either woven or non-woven composition, or any other frit construction which, when the liquid in the concentration chamber is passed through the filter, will permit passage of the plasma and not the hydrogel beads and agitator, effectively separating the plasma from the hydrogel beads and agitator as will be described in greater detail with respect to the embodiments of FIGS. 2, 6, 10, and 14 hereinafter.

FIG. 2 is a cross-sectional schematic view of a syringe embodiment of this invention for producing plasma concentrate from plasma. The syringe device 30 includes a process chamber 32 having an outer wall 34. In the process chamber 32, a plunger 36 is positioned above filter 38, the plunger and the filter 38 defining a concentrating chamber 40. The plunger has an actuator 42. The concentrator chamber 40 contains desiccated hydrogel beads 44 and an agitator 46. A concentrate chamber 48, positioned below or downstream of filter 38, includes an inlet/outlet port 50.

As with the embodiments described hereinabove, the desiccated hydrogel beads 44, actuator 42 and filter 38 can be the same as is described with respect to the device of FIG. 1. The hydrogel beads 44 can be insoluble beads or disks which will absorb a substantial volume of water and not introduce any undesirable contaminant into the plasma.

They can be dextranomer or acrylamide beads which are commercially available (Debrisan from Pharmacia and BIO-GEL P™ from Bio-Rad Laboratories, respectively). Alternatively, other concentrators can be used, such as SEPHADEX™ moisture or water absorbants (available from Pharmacia), silica gel, zeolites, cross-linked agarose, etc., in the form of insoluble inert beads or discs.

The agitator 46 can be a dense object which can be an inert metal sphere. It will be readily apparent to a person skilled in the art that the shape, composition and density of the agitator 46 can vary widely without departing from the invention so long as the agitator has a density substantially greater than whole blood. It is advantageous that the agitator be a metal sphere such as a titanium or stainless steel sphere which will not react with blood components, or an dense sphere coated with an inert coating which will not react with blood components.

The filter 38 can be any inert mesh or porous materials which will permit the passage of plasma and exclude the hydrogel beads and agitator. The filter can be a metal wire or inert fiber frit of either woven or non-woven composition, or any other frit construction which, when the liquid in the concentration chamber is passed through the filter, will permit passage of the plasma and not the hydrogel beads and agitator, effectively separating the plasma from the hydrogel beads and agitator as will be described in greater detail hereinafter.

Figure 3:
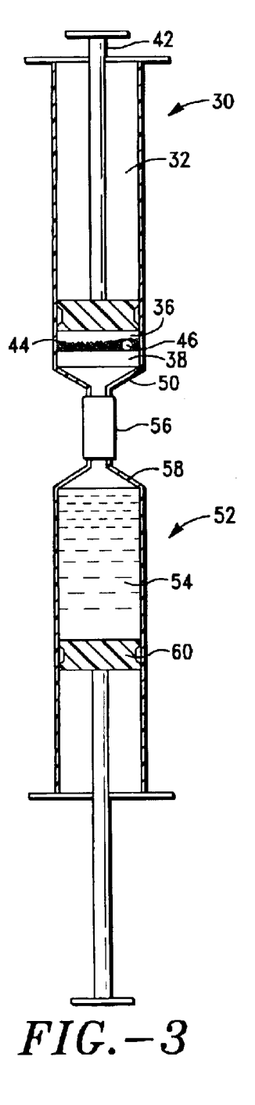
FIG. 3 is a cross-sectional schematic view of the syringe embodiment of FIG. 2 coupled with a plasma syringe filled with plasma.

FIG. 3 is a cross-sectional schematic view of the syringe embodiment of FIG. 2 after it has been coupled with a plasma syringe 52 filled with plasma 54. The inlet/outlet port 50 of the syringe of FIG. 2 communicates through coupling 56 with the inlet/outlet port 58 of the plasma transport syringe 52. Movement of plunger 60 toward the inlet/outlet port 58 displaces the plasma 54 through the coupling and inlet/outlet port 50 and through the filter 38 into contact with the desiccated hydrogel beads 44 to the position shown in FIG. 4. Alternatively, the plunger 36 can be moved away from the filter 38, drawing plasma 54 from the syringe 52 into the concentration chamber 32.

Reciprocal motion of the syringes along their vertical axis moves the agitator 46 through the plasma-hydrogel mixture, stirring the mixture to minimize gel polarization and facilitating transfer of water from the plasma into the hydrogel beads 44.

Figure 4:
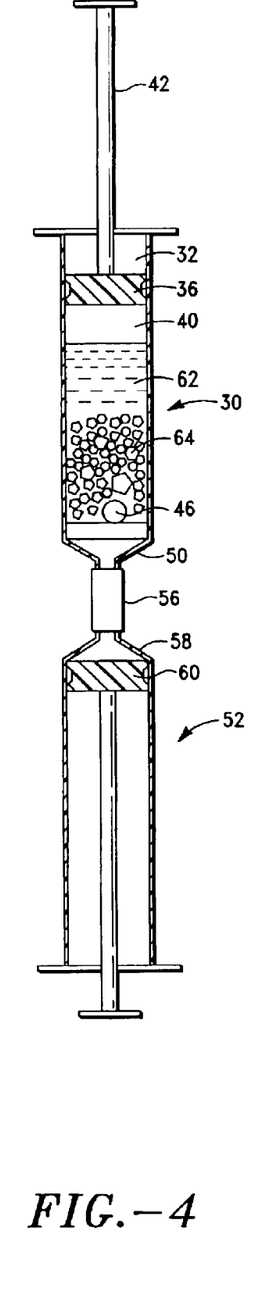
FIG. 4 is a cross-sectional schematic view of the syringe embodiment of FIG. 2 after plasma has been transferred to its concentrating chamber from the plasma syringe.

FIG. 4 is a cross-sectional schematic view of the syringe embodiment of FIG. 2 after the plasma transferred to its concentrating chamber 40 from the plasma syringe 52 has been concentrated by removal of water from the plasma. The resulting plasma concentrate 62 and hydrated hydrogel beads 64 form a mixture in the concentration chamber.

Figure 5:
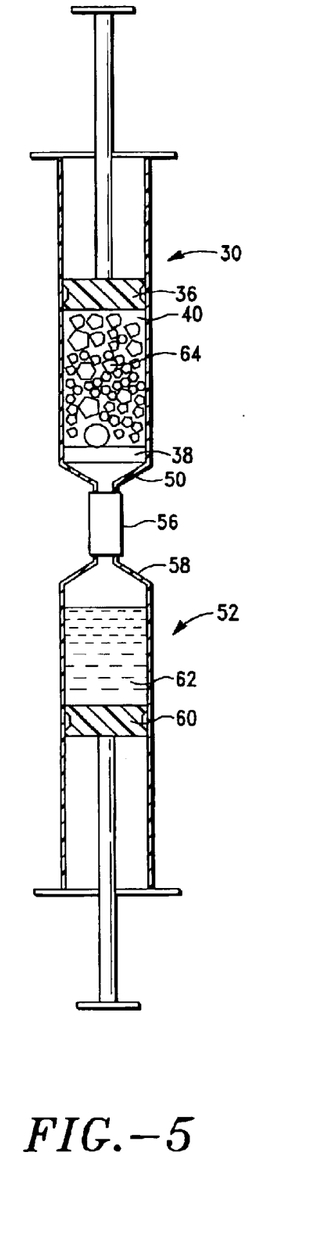
FIG. 5 is a cross-sectional schematic view of the syringe embodiment of FIG. 2 after plasma concentrate has been transferred to a plasma concentrate syringe.

FIG. 5 is a cross-sectional schematic view of the syringe embodiment of FIG. 2 after plasma concentrate 62 has been transferred to the plasma syringe 54 from the concentrate or chamber 40 by movement of the plunger 36 toward the filter 38 or movement of the plunger 60 in a direction away from the inlet/outlet port 58. The plasma syringe 52 now carrying the plasma concentrate is removed from the coupling 56 and taken to the physician for use. Alternatively, a clean plasma concentrate syringe (not shown) can be used for removal of the plasma concentrate.

Figures 6, 7, 8, 9:
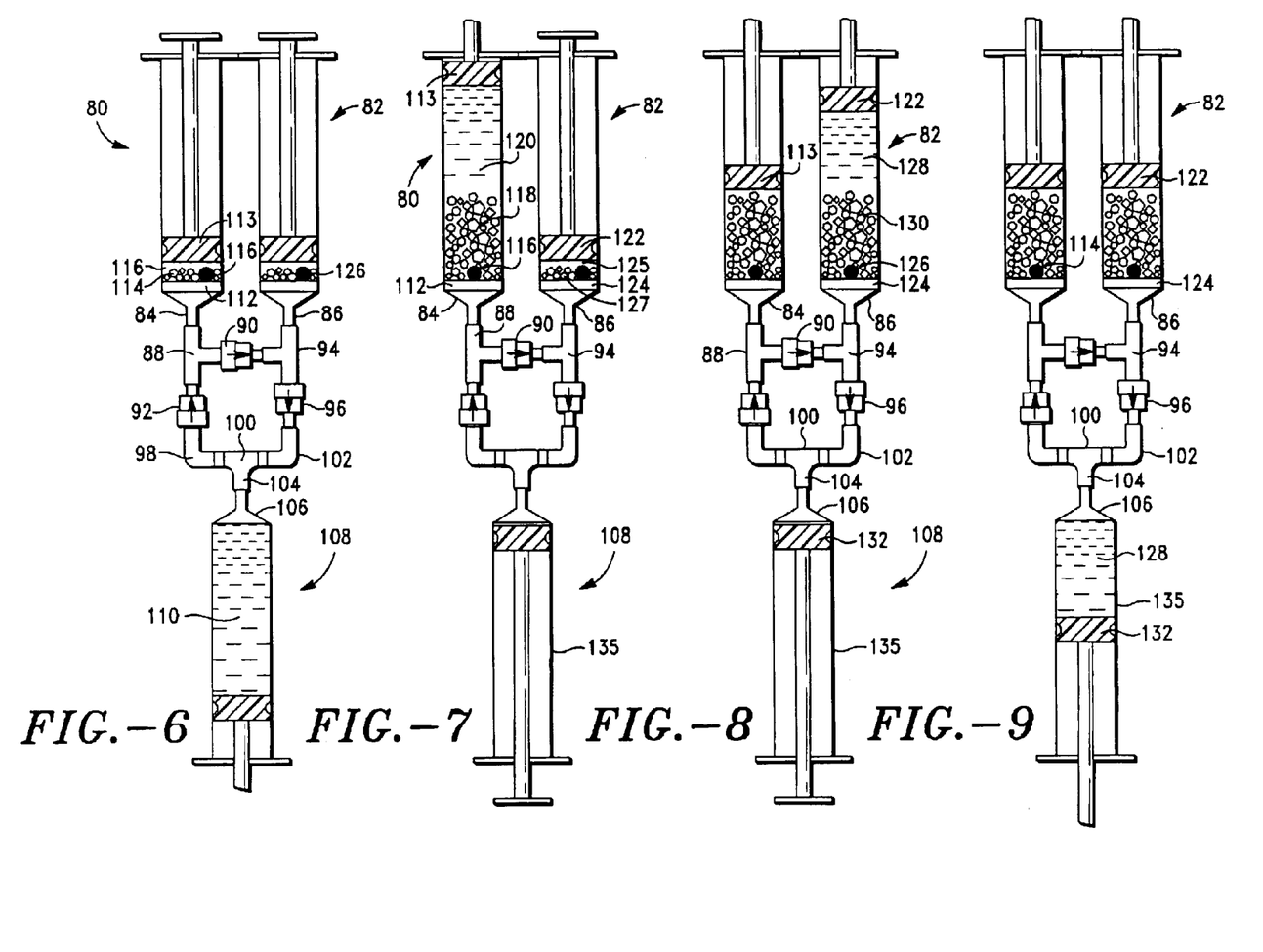
FIG. 6 is a cross-sectional schematic view of a two stage check valve syringe embodiment of this invention for producing plasma concentrate from plasma.
FIG. 7 is a cross-sectional schematic view of the two stage check valve syringe embodiment of FIG. 6 after plasma has been transferred from the plasma syringe to the concentrating chamber of a first concentrator syringe.
FIG. 8 is a cross-sectional schematic view of the two stage check valve syringe embodiment of FIG. 6 after transfer of first stage plasma concentrate from the first concentrator syringe to the concentrating chamber of a second concentrator syringe.
FIG. 9 is a cross-sectional schematic view of the two stage check valve syringe embodiment of FIG. 6 after transfer of second stage plasma concentrate from the second concentrator syringe to the plasma concentrate syringe.
Figures 10, 11, 12, 13:
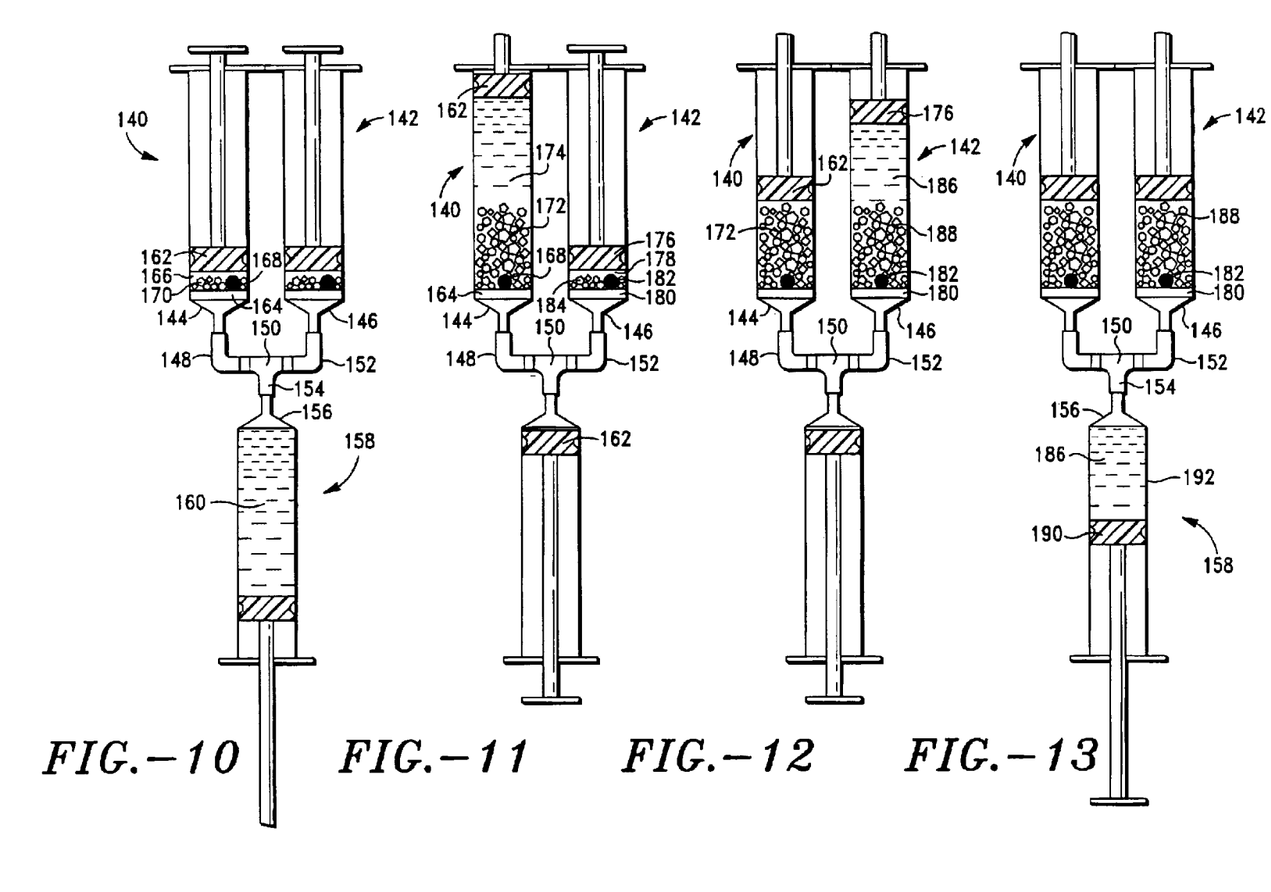
FIG. 10 is a cross-sectional schematic view of a two stage open channel syringe embodiment of this invention for producing plasma concentrate from plasma.
FIG. 11 is a cross-sectional schematic view of the two stage open channel syringe embodiment of FIG. 10 after plasma has been transferred from the plasma syringe to the concentrating chamber of a first concentrator syringe.
FIG. 12 is a cross-sectional schematic view of the two stage open channel syringe embodiment of FIG. 10 after transfer of first stage plasma concentrate from the first concentrator syringe to the concentrating chamber of a second concentrator syringe.
FIG. 13 is a cross-sectional schematic view of the two stage open channel syringe embodiment of FIG. 10 after transfer of second stage plasma concentrate from the second concentrator syringe to the plasma concentrate syringe.
Figure 14:
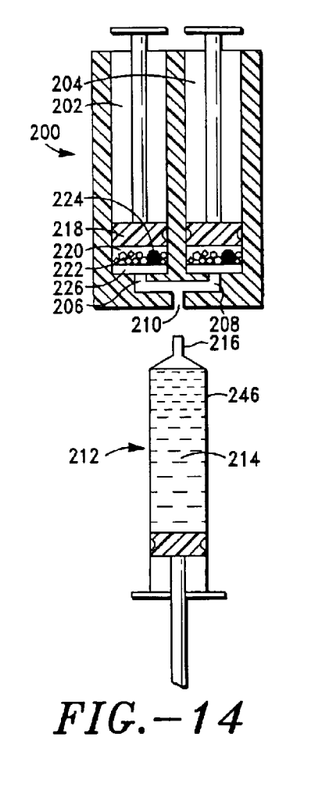
FIG. 14 is a cross-sectional schematic view of a two stage open channel integral syringe embodiment of this invention for producing plasma concentrate from plasma before the concentrator syringes are coupled to a plasma transfer syringe.

FIG. 6 is a cross-sectional schematic view of a two stage check valve syringe embodiment of this invention for producing plasma concentrate from plasma, the concentrator syringes being coupled to a plasma transfer syringe filled with plasma. This apparatus and the alternative embodiments shown in FIGS. 10 and 14 provide a two stage concentration device which, by successive concentrations, can reach a higher concentration of plasma than can be easily obtained with the single stage systems shown in FIGS. 1 and 2. For some applications, greater strength and adhesive values provided by the double concentrated plasma is desired, although a single stage concentrated product is satisfactory for most purposes. Single stage concentration can provide up to a 2.5 times (2.5×) concentration while a two stage concentration process can provide up to a 5 times (5×) concentration.

The apparatus of FIG. 6 comprises first stage syringe 80 and second stage syringe 82, each syringe having the same components and structure as the syringe 30 of FIG. 2. The inlet/outlet port 84 of the first stage syringe 80 communicates with a tee coupling 88, one conduit of which communicates with one-way check valve 90 and the other conduit of which communicates with one-way check valve 92. The inlet/outlet port 86 of the second stage syringe 82 communicates with a tee coupling 94, one conduit of which communicates with one-way check valve 90 and the other conduit of which communicates with one-way check valve 96. The check valve 92 communicates with one leg 98 of tee coupling 100, and check valve 96 communicates with a second leg 102 of tee coupling 100. The third leg 104 of tee coupling 100 is a coupling junction for the inlet/outlet port 106 of plasma transfer syringe 108.

Check valve 90 permits one-way liquid flow from tee 88 to tee 94 and prevents flow in the reverse direction from tee 94 to tee 88. Check valve 92 permits one-way liquid flow from tee 100 to tee 88 and prevents flow in the reverse direction from tee 88 to tee 100. Check valve 96 permits one-way liquid flow from tee 94 to tee 100 and prevents flow in the reverse direction from tee 100 to tee 94. The function of the check valves in directing liquid flow will become clearer in the description of the process shown in FIGS. 6–9.

FIG. 7 is a cross-sectional schematic view of the two stage check valve syringe embodiment of FIG. 6 after plasma has been transferred from the plasma syringe 108 to the concentrating chamber of a first concentrator syringe 80, and water has been absorbed by the hydrogel beads yielding a mixture of hydrated beads 118 and first stage plasma concentrate 120.

Referring to FIG. 6 and FIG. 7, the plasma transfer syringe 108 is filled with plasma 110. Movement of the plunger 113 of the first stage syringe 80 in a direction away from the filter 112 pulls the plasma 110 through the third leg 104, first leg 98, check valve 92, coupling 88, inlet/outlet port 84, filter 112 and into the concentrating chamber of syringe 80. As described with respect to FIGS. 3 and 4, reciprocal movement of the syringe 80 moves the agitator 116 through the hydrogel bead 114—plasma mixture, minimizing gel polarization and facilitating water extraction from the plasma into the hydrogel beads.

Syringe 82 has a concentrating chamber 125 defined by plunger 122 and filter 124, the concentration chamber containing hydrogel beads 127 and agitator 126.

FIG. 8 is a cross-sectional schematic view of the two stage check valve syringe embodiment of FIG. 6 after transfer of first stage plasma concentrate from the first concentrator syringe 80 to the concentrating chamber of a second concentrator syringe 82. Referring to FIG. 8 and FIG. 9, depression of the plunger 132 and/or movement of plunger 122 in a direction away from filter 124 causes movement of the first stage plasma concentrate 120 (FIG. 7) through inlet/out port 84, tee 88, check valve 90, tee 94, inlet/outlet port 86, filter 124 into the concentrating chamber of syringe 82 and into contact with hydrogel beads 125 (FIG. 7). As described above, reciprocal movement of the syringe 82 moves the agitator 126 through the hydrogel bead-plasma concentrate mixture, minimizing gel polarization and facilitating water extraction from the plasma into the hydrogel beads and forming a mixture of the second stage plasma concentrate 128 and hydrated hydrogel beads 130.

FIG. 9 is a cross-sectional schematic view of the two stage check valve syringe embodiment of FIG. 6 after transfer of second stage plasma concentrate from the second concentrator syringe 82 to the plasma concentrate syringe 132. Depression of plunger 122 toward the filter 124 displaces second stage plasma concentrate 128 (FIG. 8) through filter 124, inlet/outlet port 86, tee 94, check valve 96, second leg 102, tee 104, inlet/outlet port 106 of syringe 108 and into the barrel 135 of the plasma concentrate syringe 108. The plasma concentrate syringe 108 carrying the plasma concentrate 128 is uncoupled from the tee 100 and taken to the physician for use. Alternatively, a clean plasma concentrate syringe (not shown) can be used for removal and movement of the plasma concentrate.

The filters 114 and 124, the hydrogel beads 114 and 127, and agitators 116 and 226 of FIGS. 6–9 are described in detail with respect to FIG. 2.

FIG. 10 is a cross-sectional schematic view of a two stage open channel syringe embodiment of this invention for producing plasma concentrate from plasma, plasma-platelet mixtures or whole blood, the concentrator syringes being coupled to a plasma transfer syringe filled with plasma.

The apparatus of FIG. 10 comprises first stage syringe 140 and second stage syringe 142, each syringe having the same components and structure as the syringe 30 of FIG. 2. The inlet/outlet port 144 of the first stage syringe 140 communicates with a first leg 148 of a tee coupling 150. The inlet/outlet port 146 of the second stage syringe 142 communicates with the second leg 152 of the tee coupling 150. The third leg 154 of tee coupling 150 is a coupling junction for the inlet/outlet port 156 of plasma transfer syringe 158.

In this embodiment, check valves are omitted, and the direction of plasma flow from one syringe to the other is controlled entirely by selective movement of the respective plungers.

Referring to FIG. 10 and FIG. 11, the plasma transfer syringe 158 is filled with plasma 160. Movement of the plunger 162 of the plasma transfer syringe 140 in a direction away from the filter 164 pulls the plasma 160 through the third leg 154, first leg 148, inlet/outlet port 144, filter 164 and into the concentrating chamber 166 of syringe 140. As described with respect to FIGS. 3 and 4, reciprocal movement of the syringe 140 moves the actuator 168 through the hydrogel bead 170—plasma mixture, minimizing gel polarization and facilitating water extraction from the plasma into the hydrogel beads.

FIG. 11 is a cross-sectional schematic view of the two stage open channel syringe embodiment of FIG. 10 after plasma has been transferred from the plasma syringe 158 to the concentrating chamber 166 of a first concentrator syringe 140, and water has been absorbed by the hydrogel beads 170 yielding a mixture of hydrated beads 172 and first stage plasma concentrate 174.

FIG. 12 is a cross-sectional schematic view of the two stage open channel syringe embodiment of FIG. 11 after transfer of first stage plasma concentrate 174 from the first concentrator syringe 140 to the concentrating chamber 178 of a second concentrator syringe 142. Referring to FIG. 11 and FIG. 12, movement of plunger 176 in a direction away from filter 180 causes movement of the first stage plasma concentrate 174 through filter 164, separating the plasma concentrate from the hydrogel beads and agitator, and then through inlet/out port 144, first leg 148, tee 150, second leg 152, inlet/outlet port 146, filter 180 into the concentrating chamber 178 of syringe 142. As described above, reciprocal movement of the syringe 142 moves the actuator 182 through the hydrogel bead 184—plasma concentrate mixture, increasing the rate of water extraction from the plasma into the hydrogel beads 184 and forming a mixture of the second stage plasma concentrate 186 and hydrated hydrogel beads 188.

FIG. 13 is a cross-sectional schematic view of the two stage check valve syringe embodiment of FIG. 12 after transfer of second stage plasma concentrate 186 from the second concentrator syringe 142 to the plasma syringe 158.

Referring to FIG. 12 and FIG. 13, movement of plunger 190 in a direction away from inlet/outlet port 156 draws second stage plasma concentrate 186 through filter 180, inlet/outlet port 146, second leg 152, tee 150, third leg 154, inlet/outlet port 156 and into the barrel 192 of the plasma syringe 158. The plasma concentrate syringe 158 carrying the plasma concentrate 186 is uncoupled from the tee 150 and taken to the physician for use. Alternatively, a clean plasma concentrate syringe (not shown) can be used for removal of the plasma concentrate.

The filters 164 and 180, the hydrogel beads 170 and 184, and agitators 168 and 182 of FIGS. 10–13 are described in detail with respect to FIG. 2.

FIG. 14 is a cross-sectional schematic view of a two stage open channel integrated concentrator housing embodiment of this invention for producing plasma concentrate from plasma, plasma-platelet mixtures or whole blood before the concentrator syringes are coupled to a plasma transfer syringe.

The apparatus of FIG. 14 comprises a plasma concentrator housing 200 with a integral first concentrating chamber 202 and a integral second concentrating chamber 204. Positioned in each chamber are the functional components of the syringe 30 of FIG. 2, integrated into a unitary system. The inlet/outlet conduit 206 of the first concentrating chamber 202 communicates with the inlet/outlet conduit 208 of the second concentrating chamber 204 and with the plasma transfer syringe junction 210.

In this embodiment, the direction of plasma flow from the plasma transfer syringe to the first concentrating chamber, from the first concentrating chamber to the second concentrating chamber, and from the second concentrating chamber to the plasma transfer syringe is controlled entirely by selective movement of the respective plungers as described in detail hereinafter.

In FIG. 14, the plasma transfer syringe 212, filled with plasma 214, has an inlet/outlet port 216. The first concentrating chamber 202 has a plunger 218 and a concentrating bead chamber 220, hydrogel beads 222, an agitator 224, and a filter 226. Movement of the plunger 218 in a direction away from the filter 226 pulls the plasma 214 through the inlet/outlet port 216, plasma transfer syringe junction 210, first leg 206, filter 226 and into the concentrating chamber 220. As described with respect to FIGS. 3 and 4, reciprocal movement of the unit 200 along the central axis of the concentration chambers moves the actuator 224 through the hydrogel bead 222—plasma mixture, minimizing gel polarization and facilitating water extraction from the plasma into the hydrogel beads.

Figure 15:
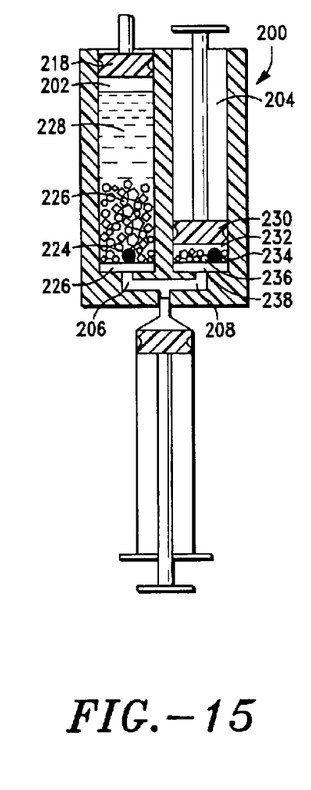
FIG. 15 is a cross-sectional schematic view of a two stage open channel integral syringe embodiment of FIG. 14 after coupling of the plasma transfer syringe and transfer of plasma to a first concentrating chamber.

FIG. 15 is a cross-sectional schematic view of the two stage open channel integrated housing embodiment of FIG.

14 after plasma has been transferred from the plasma transfer syringe 212 to the concentrating bead chamber 220, and water has been absorbed by the hydrogel beads 222 yielding a mixture of hydrated beads 236 and first stage plasma concentrate 228.

The second concentrating chamber 204 has a plunger 230 and a concentrating bead chamber 232, an agitator 234, hydrogel beads 236 and a filter 238.

Figure 16:
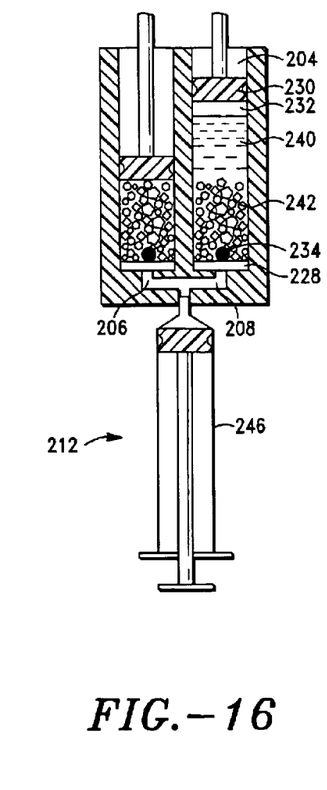
FIG. 16 is a cross-sectional schematic view of a two stage open channel integral syringe embodiment of FIG. 14 after transfer of first stage plasma concentrate to the concentration chamber of a second concentrating chamber.

Referring to FIG. 15 and FIG. 16, movement of plunger 230 in a direction away from filter 238 causes movement of the first stage plasma concentrate 228 through filter 226, separating the plasma concentrate from the hydrogel beads and agitator, and then through first leg 206, second leg 208, filter 238 and into the concentrating bead chamber 232 of concentrating chamber 204. As described above, reciprocal movement of the syringe housing 200 along the central axis of the concentrating chambers 202 and 204 moves the actuator 234 through the hydrogel bead 236—plasma concentrate mixture, minimizing gel polarization and facilitating water extraction from the plasma into the hydrogel beads 236, and referring to FIG. 6, forming a mixture of the second stage plasma concentrate 240 and hydrated hydrogel beads 242.

FIG. 16 is a cross-sectional schematic view of the two stage open channel integrated housing embodiment of FIG. 15 after transfer of second stage plasma concentrate 240 from the second concentrating chamber 232 to the plasma transfer syringe 212.

Figure 17:
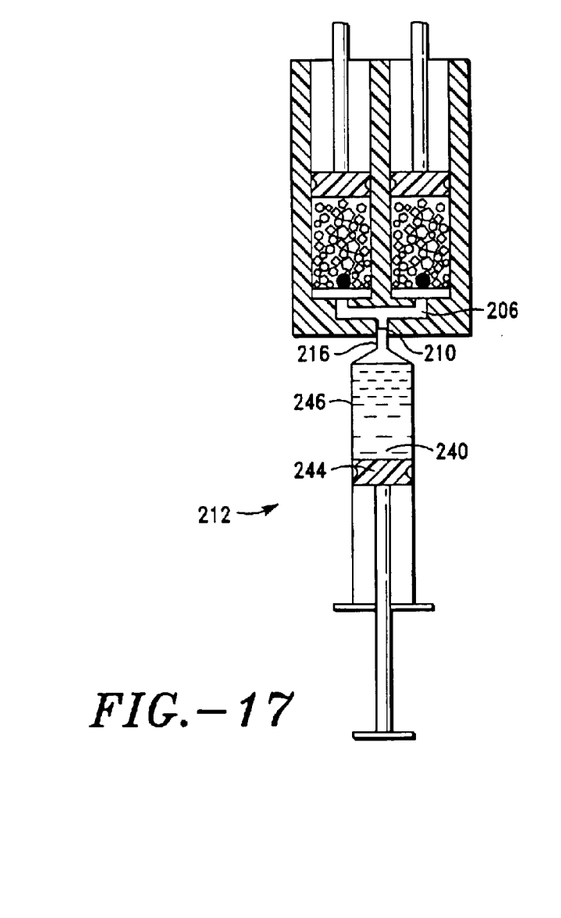
FIG. 17 is a cross-sectional schematic view of a two stage open channel integral syringe embodiment of FIG. 14 after transfer of plasma concentrate from the second concentrating chamber to the plasma concentrate syringe.

Referring to FIG. 16 and FIG. 17, movement of plunger 244 of the plasma transfer syringe 212 in a direction away from the inlet/outlet port 216 draws second stage plasma concentrate 240 through filter 228, second leg 208, syringe junction 210, syringe inlet/outlet port 216 (FIG. 17) and into the barrel 246 of the plasma transfer syringe 212.

FIG. 17 is a cross-sectional schematic view of the two stage open channel integrated housing embodiment of FIG. 16 after the second stage plasma concentrate 240 has been moved to the plasma transfer syringe 212. Alternatively, a clean plasma concentrate syringe (not shown) can be used for removal and transfer of the plasma concentrate.

Figure 18:
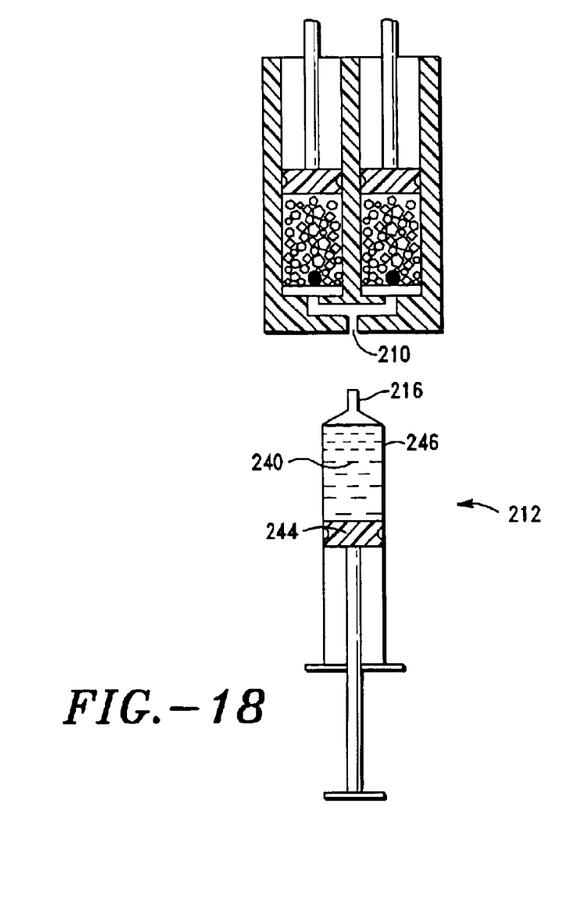
FIG. 18 is a cross-sectional schematic view of a two stage open channel integral syringe embodiment of FIG. 14 after decoupling of the plasma concentrate syringe, carrying plasma concentrate, from the integral syringe concentrator.

FIG. 18 is a cross-sectional schematic view of the two stage open channel integrated housing embodiment of FIG. 17 after the plasma transfer syringe 212 has been uncoupled from the junction 210, and is ready to be taken to the physician for use.

The filters 226 and 238, the hydrogel beads 222 and 236, and agitators 224 and 234 of FIGS. 14–18 are described in detail with respect to FIG. 2.

The invention claimed is:

1. A plasma concentrator for producing plasma concentrate from a plasma from which erythrocytes have been substantially removed, comprising a concentrating chamber having an inlet port and a concentrate outlet, the concentrating chamber containing hydrogel beads and at least one inert agitator; and a concentrate chamber having an inlet communicating with the concentrator outlet through a filter, and having a plasma concentrate outlet port.

2. A plasma concentrator of claim 1 wherein an agitator is a dense object.

3. A plasma concentrator of claim 2 wherein an agitator is a smooth ball having an inert surface.

4. A plasma concentrator of claim 3 wherein the agitator is a stainless steel ball.

5. A plasma concentrator of claim 1 wherein the filter is a porous frit.

6. A plasma concentrator of claim 1 comprising a syringe device, the syringe device including a syringe barrel with a proximal concentrating zone and a distal concentrate zone with an inlet/outlet port; a filter separating the concentrating zone from the concentrate zone; a plunger positioned for axial movement in the proximal portion of the concentrating zone; hydrogel beads and at least one agitator positioned in the concentrating zone between the plunger and the filter.

7. A plasma concentrator of claim 6 wherein an agitator is a dense object.

8. A plasma concentrator of claim 7 wherein an agitator is a smooth ball having an inert surface.

9. A plasma concentrator of claim 8 wherein the agitator is a stainless steel ball.

10. A plasma concentrator of claim 6 wherein the filter is a porous frit.

11. A plasma concentrator of claim 6 wherein the syringe barrel has an inner wall surface and the plunger is a piston forming a sealing engagement with said inner wall surface.

12. A plasma concentrator of claim 6 comprising first and second syringe devices, each syringe device including a syringe barrel with a proximal concentrating zone and a distal concentrate zone with an inlet/outlet port; a filter separating the proximal concentrating zone from the concentrate zone; a plunger positioned for axial movement in the proximal portion of the concentrating zone; hydrogel beads and at least one agitator positioned in concentrating zone between the plunger and the filter, the inlet/outlet port of the first syringe communicating with the inlet/outlet port of the second syringe.

13. A plasma concentrator of claim 12 wherein at least one of the inlet/outlet ports having a coupling for a plasma transfer syringe.

14. A plasma concentrator of claim 12 wherein the inlet/outlet ports communicate through a check valve.

15. A process for producing plasma concentrate from plasma from which erythrocytes have been substantially removed, comprising the steps of
  a) moving the plasma into a concentrating chamber containing hydrogel beads and an agitator to form a hydrogel bead-plasma mixture;
  b) causing the agitator to stir the hydrogel bead-plasma mixture, facilitating absorption of water by the beads from the plasma, until a hydrogel bead-plasma concentrate is formed; and
  c) separating the plasma concentrate from the hydrogel beads by passing the plasma concentrate through a filter.

16. A process of claim 15 wherein the hydrogel beads have the effective absorption capacity to remove at least 10 percent of the water from the plasma.

17. A process of claim 15 wherein the hydrogel beads have the effective absorption capacity to remove at least 25 percent of the water from the plasma.

18. A process of claim 15 wherein the hydrogel beads have the effective absorption capacity to remove at least 50 percent of the water from the plasma.

19. A process of claim 15 wherein the plasma concentrate from step (c) are further processed by the steps of
  d) moving the plasma concentrate into a second concentrating chamber containing hydrogel beads and an agitator to form a hydrogel bead-plasma mixture;
  e) causing the agitator to stir the hydrogel bead-plasma concentrate mixture, facilitating further absorption of water by the beads from the plasma concentrate, until a more concentrated hydrogel bead-plasma concentrate is formed; and
  f) separating the more concentrated plasma concentrate from the hydrogel beads by passing the more concentrated plasma concentrate through a filter.

20. A process for producing plasma concentrate with a plasma concentrator using a syringe device, the syringe device including a syringe barrel with a proximal concentrating zone and a distal concentrate zone with an inlet/outlet port; a filter separating a plunger zone from the concentrate zone; a plunger positioned for axial movement in the proximal portion of the concentrating zone; hydrogel beads and at least one agitator positioned in the concentrating zone between the plunger and the filter, the process comprising a) moving plasma from which erythrocytes have been substantially removed through the inlet/outlet port and the filter, by axial movement of the plunger in the proximal direction away from the filter;

b) moving the syringe in alternative distal and proximal directions along the central axis to stir the hydrogel bead-plasma mixture, facilitating absorption of water by the beads from the plasma, until a hydrogel bead-plasma concentrate is formed; and c) separating plasma concentrate from hydrogel beads by moving the plasma concentrate through the filter and into the concentrate chamber.

21. A process of claim 20 wherein in step (c) the plasma concentrate is moved through the filter and into the concentrate chamber by moving the plunger in the distal direction toward the filter.

22. A process of claim 21 wherein the plasma concentrate is forced through the inlet/outlet port by moving the plunger in the distal direction toward the filter.

23. A process of claim 20 wherein the hydrogel beads have the effective absorption capacity to remove at least 10 percent of the water from the plasma.

24. A process of claim 20 wherein the hydrogel beads have the effective absorption capacity to remove at least 25 percent of the water from the plasma.

25. A process of claim 20 wherein the hydrogel beads have the effective absorption capacity to remove at least 50 percent of the water from the plasma.

26. A process for producing plasma concentrate from whole blood comprising the steps of a) removing erythrocytes from whole blood to form a plasma which is substantially free from erythrocytes;

b) moving the plasma into a concentrating chamber containing hydrogel beads and an agitator to form a hydrogel bead-plasma mixture;

c) causing the agitator to stir the hydrogel bead-plasma mixture, facilitating absorption of water by the beads from the plasma, until a hydrogel bead-plasma concentrate is formed; and d) separating the plasma concentrate from the hydrogel beads by passing the plasma concentrate through the filter.

27. A process for producing plasma concentrate from whole blood using a syringe device, the syringe device including a syringe barrel with a proximal concentrating zone and a distal concentrate zone with an inlet/outlet port; a filter separating a plunger zone from the concentrate zone; a plunger positioned for axial movement in the proximal portion of the concentrating zone; hydrogel beads and at least one agitator positioned in the concentrating zone between the plunger and the filter, the process comprising a) removing erythrocytes from whole blood to form a plasma which is substantially free from erythrocytes;

b) drawing plasma from which erythrocytes have been substantially removed through the inlet/outlet port and the filter, by axial movement of the plunger in the proximal direction away from the filter;

c) moving the syringe in alternative distal and proximal directions along the central axis to stir the hydrogel bead-plasma mixture, facilitating absorption of water by the beads from the plasma, until a hydrogel bead-plasma concentrate is formed;

d) separating plasma concentrate from hydrogel beads by moving the plasma concentrate through the filter and into the concentrate chamber.

28. A process of claim 27 wherein in step (c) the plasma concentrate is moved through the filter and into the concentrate chamber by moving the plunger in the distal direction toward the filter.

29. A process of claim 27 wherein the plasma concentrate is forced through the inlet/outlet port by moving the plunger in the distal direction toward the filter.

* * * * *